United States Patent
Liu et al.

(10) Patent No.: US 8,796,487 B2
(45) Date of Patent: Aug. 5, 2014

(54) PROCESS FOR THE PREPARATION OF HIGHLY PURIFIED, DIALKYDITHIOPHOSPHINIC COMPOUNDS

(75) Inventors: Leo Zhaoqing Liu, Pennington, NJ (US); Gary Woodward, Northwich Cheshire (GB)

(73) Assignee: Rhodia Operations, Aubervilliers (FR)

( * ) Notice: Subject to any disclaimer, the term of this patent is extended or adjusted under 35 U.S.C. 154(b) by 1374 days.

(21) Appl. No.: 12/455,847

(22) Filed: Jun. 8, 2009

(65) Prior Publication Data

US 2009/0253931 A1  Oct. 8, 2009

Related U.S. Application Data

(62) Division of application No. 11/977,620, filed on Oct. 25, 2007, now Pat. No. 7,572,931.

(60) Provisional application No. 60/854,279, filed on Oct. 25, 2006.

(51) Int. Cl.
*C07F 9/34* (2006.01)
*C07F 9/30* (2006.01)

(52) U.S. Cl.
CPC .. *C07F 9/34* (2013.01); *C07F 9/301* (2013.01)
USPC ................................. 562/9; 568/14

(58) Field of Classification Search
CPC ................... C07F 9/301; C07F 9/34
USPC ................................ 562/9; 568/14
See application file for complete search history.

(56) References Cited

PUBLICATIONS

Fedorova (Zhurnal Obshchei Khimii (1982), 52(1), 214, Chem Abst. 96:181355).*

* cited by examiner

*Primary Examiner* — Fereydoun G Sajjadi
*Assistant Examiner* — Amy C Bonaparte

(57) ABSTRACT

An improved process for production of dialkyldithiophosphinic acid including sulfurizing a purified dialkylphosphinic acid by: reacting a hypophosphorous acid or salt with a stoichiometric excess of an alpha olefin in the presence of a free radical initiator to form a reaction product comprising monoalkylphosphinic acid and dialkylphosphinic acid; adding sufficient aqueous base to the reaction product to i) form the salts of the phosphinic acids, and ii) establish an aqueous phase and an organic phase, wherein a monoalkylphosphinic acid solubilizes into an aqueous phase; separating the organic phase from the aqueous phase; acidifying the organic phase and removing the olefin from the organic phase; isolating the purified dialkylphosphinic acid product; and sulfurizing the purified dialkylphosphinic acid product to form a dialkydithiophosphinic acid. The present invention also provides a process for preparing purified dialkylthiophosphinic chloride, and a process for preparing purified dialkylmonothiophosphinic acids.

10 Claims, No Drawings

PROCESS FOR THE PREPARATION OF HIGHLY PURIFIED, DIALKYDITHIOPHOSPHINIC COMPOUNDS

CROSS-REFERENCE TO RELATED APPLICATIONS

The present application relates to U.S. Provisional Patent Application No. 60/854,279, filed Oct. 25, 2006, and is a divisional application of U.S. application Ser. No. 11/977,620 filed Oct. 25, 2007, incorporated herein by reference in its entirety.

FIELD OF THE INVENTION

The present invention generally relates to an improved process for the economical production of dialkyldithiophosphinic acid compounds, preferably branched dialkyldithiophosphinic acid compounds. The process enables a single phase separation which realizes a high purity dialkylphosphinic acid product which is then converted to a dialkyldithiophosphinic acid. The present invention also provides a process for the preparation of highly purified dialkylthiophosphinic halide and products therein, thereby producing a dialkylthiophosphinic compound having one sulfur atom and one halide atom. The present invention also provides a process for the preparation of highly purified dialkylmonothiophosphinic acids and products therein, thereby producing a dialkylmonothiophosphinic acid having one oxygen and one sulfur.

BACKGROUND OF THE INVENTION

Numerous derivatives of organic phosphinic and dithiophosphinic acids are known to exist and to have considerable commercial value as well as a great variety of useful applications. For example, organic phosphinates and dithiophosphinates as well as their acids are effective wetting agents and detergents; plasticizers for many plastics and resins; bonding agents for asphalt and similar compositions; color stabilizers and oxidation inhibitors for greases and lubricants (U.S. Pat. No. 3,001,938); corrosion inhibitors; flame proofing agents; flotation auxiliaries; metal extractants; setting retarders for gypsum; and textile auxiliaries such as filament stabilizers (U.S. Pat. No. 3,374,288).

Highly purified, highly branched dialkyldithiophosphinic acids have been especially recognized as being very important and much desired precursors, intermediate products, and end products in numerous specialized fields, including mining. For example, branched dialkyldithiophosphinic acids act as metal extractants and froth flotation agents.

As a result of the above listed numerous possibilities of practical application, a demand has been created for a simple industrial synthesis for the production of dialkyldithiophosphinic acids in a highly purified state.

Because of the above described great commercial value, many methods of preparing organic phosphinic acids have been advanced. Although the methods vary widely in their individual steps, a great many employ the reactions of phosphorous-halogen compounds to attain carbon-to-phosphorous bonds. While it has long been known to be possible to form such bonds by reacting alkyl halides with phosphine, or by the use of Grignard reagents, such methods are not practical in commercial scale operations.

Stiles et al. (U.S. Pat. No. 2,724,718) discloses a process for the production of phosphinates employing the reaction between a compound containing olefinic double bonds and, preferably, a class of compounds consisting of compounds of the formula (I):

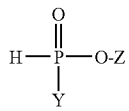

wherein Z represents a monovalent hydrocarbon radical free of aliphatic multiple bonds, or a monovalent inorganic cation, and Y represents a hydrogen atom, a monovalent hydrocarbon radical free of aliphatic multiple bonds, or the group —OZ in which Z is defined as above. Among the phosphorous classes and compounds that Stiles et al. suggest as reactants are the salts of hypophosphorous acid, hydrocarbyl esters of hypophosphorous acid, hydrocarbyl esters of organic phosphinic acids and mono- and di-hydrocarbyl esters of phosphorous acid. A particularly preferred subclass comprises the alkali metal salts of hypophosphorous acid such as sodium hypophosphite which Stiles et al. found to be able to be directly added to olefins containing up to 14 carbon atoms "to produce in a single, operational step a water soluble detergent in substantially quantitative yields."

Stiles et al. also noted that 1-olefins exhibit a somewhat higher rate of reaction in these processes than do other olefins. The Stiles et al. addition reaction is initiated by the presence of free radicals in intimate contact with the reactants. Neither the reaction temperature nor the reaction pressure is taught to be critical by Stiles et al.

Stiles et al. teach that where a mole to mole addition is desired, it is generally preferable to employ the reactants in about equimolar proportions or with the phosphorous compound in excess; and, where it is desirable to cause more than one mole of the olefinic compound to be incorporated in the product.

Dialkyldithiophosphinic acids have also been used to extract metals (U.S. Pat. No. 5,447,552). In the general procedure employed for the separation of metal elements from solutions thereof, especially acidic solutions, the feed solution generally contains nickel and/or cobalt ions. The extract containing the extracted metal(s) is usually sent to a scrubber wherein it is scrubbed with dilute acid and then sent to a stopper where it is stripped with more concentrated acid to separate the metals. Hydrochloric acid and sulfuric acid are the preferred acids of the prior art to scrub and strip the extract. Bis-(2,4,4-trimethylpentyl) dithiophosphinic acid is said to be a preferred extractant; especially for the separation of cobalt from nickel.

The currently commercialized method to manufacture dialkyldithiophosphinic acids is by direct sulfurisation of the corresponding dialkyl phosphines, these are in turn manufactured from phosphine gas and olefins under pressure. Phosphine is highly toxic and flammable and the addition of an olefin to phosphine gas often yields a mixture of primary, secondary and tertiary phosphines. In particular when a dialkyl phosphine is the desired product the process also produces undesirable amounts of trialkyl phosphines which unlike primary phosphines, cannot be recycled and, on sulfurisation, produce trialkyl phosphine sulfides as an impurity, which must be removed by extraction from the dialkyldithiophosphinic acids.

This art-recognized problem of producing high purity dialkyldithiophosphinic acids by a practical reaction process which is applicable to the production of compounds having a variety of structures, especially highly branched dialkyl structures, has heretofore remained unsolved.

Phosphinic acid was converted by reacting with thiophosphoryl chloride into thiophosphinic chloride at very low yield (33-54%, Fedorova, G K et al Zhurnal Obshchei Khimii (1982), 52(1) 214 Chem. Abst. 96:181355.

Alternatively, thiophosphinic halides can be prepared from other starting materials such as phosphines (Kaushik, M. P. et al Indian J. Chem. Sect B: Org. Chem. Med. Chem. (1991), 20B(10), 932), thiophosphonous anhydride (Bliznyuk, N. K. et al SU347332), alkaryl halide (Baranov, Yu. I. et al SU221695), phosphinic chloride (Groenweghe, L. C. C. U.S. Pat. No. 3,206,442; Kabachnik, M. I. Godovikov, N. N. Doklady Akademii Nauk SSSR (1956), 110 217 Chem abst. 51:25335), dithiophosphinic acid (Lorenz, W. Schrader, G. DE 1067017) and bis(dialkylphosphinothioyls) (Colin, R. DE 1054453).

Accordingly, it is an object of this invention to provide a practical and efficient process for addressing this technical problem of producing high purity dialkyldithiophosphinic acids by providing conditions whereby, in a straightforward alpha olefin-hypophosphorous acid or a salt thereof free radical reaction, any monoalkylphosphinic acid and other water soluble impurities present are removed from the dialkylphosphinic acid product by a simple neutralization/phase separation without the need for a third component organic solvent addition before converting the dialkylphosphinic acid to dialkyldithiophosphinic acid.

Other objects will be evident from the ensuing description and appended claims.

SUMMARY OF THE INVENTION

The present invention relates to a process wherein a straightforward synthesis of dialkylphosphinic acids, especially branched dialkylphosphinic acids and their phosphinates can be produced with high purity using standard reaction processing and apparatus, i.e., in the absence of high pressures and temperatures; and straightforward aqueous phase extraction/separation processing without the need for an additional organic solvent addition step and the attendant recovery procedures and equipment for the necessary additional solvent recovery. The purified dialkylphosphinic acid is sulfurized to yield a highly purified dialkyldithiophosphinic acid.

The improved process permits the production of dialkyldithiophosphinic acids by sulfurizing a dialkylphosphinic acid, which is made in high purity by the free radical reaction of an alpha olefin with certain phosphorus compounds wherein the olefin is used in excess in order to provide the solvent medium for the reaction product and subsequently isolating the dialkylphosphinic acid by preferentially neutralizing any monoalkylphosphinic acid by-product; extracting same with an aqueous wash; and isolating and purifying the desired dialkyl phosphinic acid from the excess olefin reactant solvent by art recognized techniques such as acidification, filtration, and distillation.

This is accomplished firstly by the use of excess alpha olefin which subsequently functions as the preferential solubility medium phase for the dialkylphosphinic acid; and secondly, by the recognition that by creating a basic pH environment, the alkali or alkali earth ester of the monoalkylphosphinic acid is significantly more soluble in the aqueous phase than in the organic phase, i.e., the excess olefin reactant phase, than the dialkylphosphinic acid ester product.

In another respect, the present invention provides an efficient process to convert dialkylphosphinic acid into dialkylthiophosphoryl halide, preferably dialkylthiophosphoryl chloride, comprising the step of reacting dialkylphosphinic acid with a halogenating agent and a sulfurizing agent to form dialkylthiophosphinic halide. For example, the present invention converts dialkylphosphinic acid into dialkylthiophosphinic chloride in a one-pot process without additional purification by reacting dialkylphosphinic acid ($R^1R^2PO_2H$) with thiophosphoryl chloride and then with phosphorus pentasulfide ($P_2S_5$) in atmospheric pressure under anhydrous conditions. The obtained product is a liquid while all the by-products are solid at room temperature. The product may be isolated by simply discharging from the reactor at a yield of about 90% or more. The remaining non-converted intermediates could be recovered after dissolving the solid in water, extracting with hexanes, vacuum dried and recycled.

In another respect, the present invention provides an efficient process to convert dialkylphosphinic acid into dialkylmonothiophosphinic in a single step without utilization of expensive or/and highly hazardous raw materials. This is achieved by reacting $R^1R^2PO_2H$ with sulfurizing agent to form a mixture, and then dissolving the mixture with aqueous acid to form a reaction product; wherein $R^1$ and $R^2$ are each independently an alkyl radical having from 2 to 22 carbon atoms; and then extracting a purified product from the reaction product by contacting the reaction product with a water-immiscible solvent. For example, this is achieved by reacting dialkylphosphinic acid ($R^1R^2PO_2H$) with phosphorus pentasulfide ($P_2S_5$) in atmospheric pressure under anhydrous conditions, and then dissolving the solution with diluted sulfuric acid. Purified product is extracted from the mixture with hexanes.

In another respect, the present invention provides a process for converting dialkylmonothiophosphinic halide into dialkylmonothiophosphinic acid comprising: reacting dialkylmonothiophosphinic halide with water as follows:

$$R^1R^2PSX + H_2O \rightarrow R^1R^2P(\!=\!S)OH + HX,$$

wherein X is a halogen, to form a mixture; wherein $R^1$ and $R^2$ are each independently an alkyl radical having from 2 to 22 carbon atoms; and then acidifying the mixture with acid to extract dialkylmonothiophosphinic acid. For example, the invention provides a process for converting dialkylmonothiophosphinic chloride into dialkylmonothiophosphinic acid comprising reacting dialkylmonothiophosphinic chloride with water in alkaline conditions and then neutralizing with an acid. The product is extracted with hexanes and recovered after evaporating the solvent.

In another respect, the present invention provides a process for converting dialkylmonothiophosphinic halide into dialkyldithiophosphinic acid comprising reacting dialkylmonothiophosphinic halide with a sulfurizing agent to form the dialkyldithiophosphinic acid. For example, the invention provides a process for converting dialkylmonothiophosphinic chloride into dialkyldithiophosphinic acid comprising reacting dialkylmonothiophosphinic chloride with sodium hydrogen sulfide or/and sodium sulfide in water, followed by neutralization with sulfuric acid, hexane extraction to obtain the product.

DETAILED DESCRIPTION OF THE PREFERRED EMBODIMENTS

The subject of the present invention is an improved process for the preparation of organophosphorous chemicals particularly useful in mining applications. More specifically the invention relates to a process for the preparation of alkyl thiophosphinate metal extractants by sulfurizing a purified dialkylphosphinic acid of the formula (I):

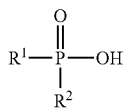

(I)

wherein $R^1$ and $R^2$ are each independently, i.e., either identical or different, an alkyl radical having from 2 to 22 carbon atoms, these radicals optionally substituted, preferably di- or higher substituted by chloro, bromo, alkyl or alkoxy groups or mixtures thereof, each alkyl or alkoxy group individually having from 1 to 4 carbon atoms. Formula (I) is synthesized by a dialkyl purification process as described in U.S. Pat. No. 7,049,463, which is hereby incorporated by reference in its entirety. Namely, formula (I) is synthesized by the free radical enhanced reaction of hypophosphorous acid or its salts with a stoichiometric excess of an alpha olefin. Then the dialkylphosphinic acid reaction product is isolated and purified by adding an aqueous base solution that has been found to preferentially neutralize any monoalkylphosphinic acid by-product formed by the reaction. The monoalkyl phosphinic acid, being more soluble in the aqueous phase than in the organic phase where the dialkylphosphinic acid is preferentially solubilized, is easily separated from the dialkylphosphinic acid product. Optionally, for higher purification of the dialkylphosphinic acid, additional purification steps well known by those skilled in the art may be used, such as a subsequent acidification and distillation.

In this manner, unwanted impurities, such as unreacted alkenes, water, or other volatiles can be easily removed from the dialkyl product.

Preferably $R^1$ and $R^2$ are identical.

In a preferred embodiment, the alpha olefins used in the dialkyl purification process contain from 2 to 22 carbon atoms, preferably from 2 to 12 carbon atoms and most preferably from 2 to 10 carbon atoms. In the process of the invention, although straight-chain alpha mono-olefins can be used, preferably the alpha mono olefins are branched, and more preferably highly branched. Examples of such olefins include: ethylene, propene, butene-(1), hexane-(1), octane-(1), dodecene-(1), tetradecene-(1), hexadecene-(1), octadecene-(1), heneicosene-(1), docosene-(1), 2-methylpentene-(1), 2-ethyl-hexene-(1), and diisobutylene-(1). Also mixtures of such olefins may be used.

The alpha-olefins selected as starting compounds in the instant process are obtained by processes well known in the art including the cracking of petroleum distillates or waxes, by splitting off hydrochloric acid from paraffins with terminal chlorine atoms, or by dehydration of alcohols with a terminal hydroxyl group.

The reaction initiator compound may be any compound that readily dissociates either 1) under the influence of temperature, preferably between about 24° C. and 200° C. and/or 2). actinic light. As free radical forming agents in the process of the invention, all known radical forming substances may be used, for example: positive halogen compounds such as calcium hypochlorite, sodium N-chloro-p-toluenesulfonamide, and sodium N-chlorobenzenesulfonamide; metallo-alkyl compounds such as lead tetraethyl and lead tetraphenyl; carbonyl compounds such as acetone, methyl ethyl ketone, and benzaldehyde; and the organic peroxides such as di-tertiary-butyl peroxide, tertiary-butyl hydroperoxide, di-cumylperoxide, benzoylperoxide; tertiary-butyl perbenzoate, 2,5-dimethyl-bis-2,5-(peroxybenzoate), 2,2-bis(tertiary-butylperoxy)butane and benzoyl peroxide. Advantageously, di-tert-butylperoxide may be used.

The radical forming agent(s) is used in catalytically effective amounts and may be varied over wide limits depending on the character of the particular initiator. In general, usually from about 0.5 mole percent to about 10 mole percent of reaction initiator, based on the phosphorus reactant, is suitable.

In order to solubilize the free radical initiator in the reaction mixture, it may be necessary to add an inert solvent as a dissolving agent. It is preferable, however, that the free radical initiator be selected so that it is able to be dissolved in at least one of the reactants; i.e., the alpha olefin, the hypophosphorous acid or a salt thereof. All of the free radical initiator-reactant composition can be added at the beginning of the reaction or added subsequently in portions into the reaction vessel.

In the situation wherein the reaction is started by ultraviolet radiation, the reaction solution should be exposed to direct radiation by an ultraviolet lamp.

It may be necessary to add a transition metal catalyst to further improve the reaction rate.

The dialkylphosphinic acid reaction is advantageously carried out as follows: The alpha olefin, optionally mixed with catalytic amounts of a radical forming agent, is introduced into hypophosphorous acid or a salt thereof. The reaction should occur in the presence of an excess of the alpha olefin, i.e., the ratio of the olefin to the hypophosphorous acid or its salt should be greater than 2 to 1; preferably greater than 2.5 to 1. The presence of acid has been found to have a positive effect on the yield of the dialkylphosphinic acids in olefin phosphination reactions. Preferably the reaction takes place in the presence of a yield enhancing effective amount of an acid(s). Suitable acids are inorganic as well as organic acids insofar as they do not decompose or cause negative side reactions under the primary reaction conditions. Suitable examples are hydrochloric acid, sulfuric acid, and/or, most preferably, acetic acid. The reaction may also be carried out in the presence of inert solvents, for example alcohols, esters, or hydrocarbons, such as benzene. However, it is preferred to conduct the reaction in the absence of any additional solvent component.

When the initial reaction is completed, water may be added to adjust the viscosity of the product composition for ease in subsequent processing.

The temperature employed in the process of this invention can be varied depending on factors known to those skilled in the art. Reaction will generally be carried out at temperatures within the range of from about 24° C. to about 200° C. and reaction temperatures of from about 100° C. to about 150° C. are particularly preferred. In the most preferred embodiments of the invention, the reaction is conducted at a temperature of from about 110° C. to about 140° C.

The reaction may be carried out at atmospheric pressure or above atmospheric pressure in a sealed vessel.

The process of this invention is conducted for a period of time sufficient to produce the desired compound in adequate yield. Reaction times are influenced to a significant degree by the reaction temperature; the concentration and choice of reactants; and other factors known to those skilled in the art. In general, reaction times can vary from 8 hours to several days or longer.

If the alpha olefin is initially used in its pure form, the excess alpha olefin can be recycled.

The process of this invention is preferably conducted in a batch or semi-continuous fashion. The reaction can be conducted in a single reaction zone or in a plurality of reaction zones or it may be conducted intermittently in an elongated tubular zone or series of such zones. The materials of construction employed should be inert to the reactants during the reaction and the equipment should be fabricated such that it is able to withstand the reaction temperatures and pressures.

To enhance separation and purification of the dialkylphosphinic acid from the monoalkylphosphinic acid by-product and other undesirable impurities, the organic phase may be intimately washed with a basic solution, preferably caustic, which preferentially neutralizes the monoalkylphosphinic acid. The resulting aqueous layer, in which the monoalkylphosphinic acid is highly soluble, is removed. The dialkylphosphinic acid product can be further isolated from the reaction mixture and purified by well-known, art recognized techniques such as fractional distillation, the wipe film evaporation, and/or conventional washing techniques. Preferably, to further purify the desired dialkylphosphinic acid product, which is solubilized in the organic medium phase, primarily the alpha olefin reactant which was originally added to the reaction vessel in excess, the organic phase is acid washed, preferably with an inorganic acid such as sulfuric acid. The aqueous phase is again removed and the organic phase filtered and distilled to remove any final impurities and volatile materials.

It has been discovered that a highly purified dithiophosphinic acid of general formula (II) may be formed by sulfurizing the highly purified dialkylphosphinic acid formed by the above process.

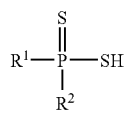

(II)

wherein $R^1$ and $R^2$ are each independently, i.e., either identical or different, an alkyl radical having from 2 to 22 carbon atoms, these radicals optionally substituted, preferably di- or higher substituted by chloro, bromo, alkyl or alkoxy groups or mixtures thereof, each alkyl or alkoxy group individually having from 1 to 4 carbon atoms.

This invention proposes to sulfurize the dialkylphosphinic acid in a non-reductive process, however, any suitable sulfurization process may be used. The reverse reaction, i.e., heating the dithiophosphinic acid with water/oxygen to yield phosphinic acid, is also true.

The following chemistries of Formulas III and IV have been observed.

$$R^1R^2POOH+PSCl_3 \rightarrow R^1R^2PSCl \qquad (III),$$

and $$R^1R^2POCl+NaSH \rightarrow R^1R^2P(=S)OH+NaCl \qquad (IV).$$

These indicate that the P=O bond can be replaced by P=S under non reductive conditions. Suitable sulfurization agents include, but are not limited to, elemental sulfur, sulfur chlorides, and $P_2S_5$.

In another embodiment sulfurization may be obtained by sulfurization chemistry which uses a reducing agent such as $LiAlH_4$ or $Cl_3SiH$ or $Ph_2SiH_2$ followed by treatment of the phosphine obtained with sulfur, usually in the same reactor. Reducing agents such as $Cl_3SiH$ or a silane may, for example, be used.

Preferred dialkyldithiophosphinic acids formed in accordance with the invention include, but are not limited to, bis-(2,4,4-trimethylpentyl) dithiophosphinic acid; dithiophosphinate, dithiophosphinate blends.

In another respect, the present invention provides an efficient process to convert dialkylphosphinic acid into dialkylthiophosphoryl halide, preferably dialkylthiophosphoryl chloride, comprising the step of reacting dialkylphosphinic acid with a halogenating agent and a sulfurizing agent to form dialkylthiophosphinic halide.

The halogenation agent and sulfurizarion agent are provided by a single reagent compound or separate reagent compounds.

Typical halogenizing agents include but are not limited to dihalogen (for e.g. $Cl_2$, $Br_2$, $I_2$, $F_2$) together with phosphorus trihalide, phosphorus pentahalide, thiophosphoryl halide, phosphorus oxytrihalide, thionyl di-halide, sulfur halogen compounds for example $SCl_2$, $S_2Cl_2$, $SF_6$, $COCl_2$, thiophosgene, metal halides for example $AlCl_3$, $SnCl_2$, $SiCl_4$, $FeCl_3$, $BF_3$ etc.

Typical sulfurizing agents include but are not limited to phosphorus sulfide for example, $P_2S_5$, $P_4S_6$, $P_4S_7$, thiophosphoryl halides $PSX_3$ (X=halogen), sulfur halogen compounds for example $SX_2$, $S_2X_2$, $SF_6$, elemental sulfur with an oxidizing agent, phosphorus oxysulfides for example $P_2O_3S_2$, $P_2O_2S_3$.

For example, the present invention provides a preferred process for successfully converting pure dialkylphosphinic acid into highly pure dialkylthiophosphinic chloride in an economic way as follows in Formula V:

$$R^1R^2POOH+PSCl_3+P_2S_5 \rightarrow R^1R^2PSCl+byproducts \qquad (V).$$

In Formula V, $R^1$ and $R^2$ are each independently an alkyl radical having from 2 to 22 carbon atoms or as otherwise defined above.

Given the availability of highly pure dialkylphosphinic acid, it is attractive to have this efficient process of Formula V to convert it into dialkylthiophosphoryl chloride. Preferably, the dialkylphosphinic acid is converted into dialkylthiophosphinic chloride in a one-pot process without an additional purification step. This is achieved by reacting dialkylphosphinic acid ($R^1R^2PO_2H$) with thiophosphoryl chloride and then with phosphorus pentasulfide ($P_2S_5$) in atmospheric pressure under anhydrous conditions. Advantageously, the obtained product is a liquid while all the by-products are solid at room temperature. The product is isolated by simply discharging from the reactor at a yield about 90% or more. The remaining non-converted intermediates are recovered after dissolving the solid in water, extracting with hexanes, vacuum dried and recycled.

In a particularly preferred embodiment of the process about 100 parts by weight bis(2,4,4-trimethylpentyl)phosphinic acid and 20 to 70 parts by weight thiophosphoryl chloride are heated under dry nitrogen at about 80 to about 160° C. for about 1 to 5 hours. Then 5 to 50 parts by weight phosphorus pentasulfide is added. The reaction temperature is increased to about 140° C. over about 0.1 to 2 hours and then kept at about 100 to about 160° C. for about 1 to 8 hours. Precipitation occurred about 1 hour after phosphorus pentasulfide addition. After about 1 to 3 hours of reaction, 0.2 to 1 parts by weight more of phosphorus pentasulfide is added and then excess thiophosphoryl chloride is stripped out of the reaction under slightly vacuum. The batch is left to cool to room temperature and the liquid is decanted and the remaining product is washed out with hexanes to yield the product. The solid was dissolved with about 20 to 200 parts by weight of 1% sulfuric acid in water and extracted with hexanes to yield a mixture of the product, byproducts and non-converted bis(2,4,4-trimethylpentyl)phosphinic acid. This can be reused with fresh bis(2,4,4-trimethylpentyl)phosphinic acid.

In another respect, the present invention provides an efficient process to convert dialkylphosphinic acid into dialkylmonothiophosphinic in a single step without utilization of expensive or/and highly hazardous raw materials. This is achieved by reacting $R^1R^2PO_2H$ with sulfurizing agent to form a mixture, and then dissolving the mixture with aqueous acid to form a reaction product; wherein $R^1$ and $R^2$ are each independently an alkyl radical having from 2 to 22 carbon atoms or as otherwise defined above; and then extracting a purified product from the reaction product by contacting the reaction product with a water-immiscible solvent.

Typical sulfurizing agents include but are not limited to phosphorus sulfide for example, $P_2S_5$, $P_4S_6$, $P_4S_7$, thiophosphoryl halides $PSX_3$ (X=halogen), sulfur halogen compounds for example $SX_2$, $S_2X_2$, $SF_6$, elemental sulfur with an oxidizing agent, phosphorus oxysulfides for example $P_2O_3S_2$, $P_2O_2S_3$.

Typical acids include but are not limited to sulfuric acid, mineral acids such as HX (X=halogen), nitric acid, $H_2CO_3$, soluble organic carboxyl and sulphonic acids, phosphonic acids, hypophosphorous acid, phosphoric acid, phosphorous acid, and polyacids such as polyacrylic, vinylsulfonic or acidic water soluble co-polymers.

For example, the present invention provides a preferred method for successfully converting dialkylphosphinic acid into dialkylmonothiophosphinic in a single step without utilization of expensive or/and highly hazardous raw materials as follows in Formula VIa followed by Formula VIb.

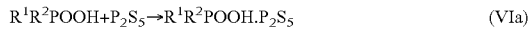

$$R^1R^2POOH+P_2S_5 \rightarrow R^1R^2POOH.P_2S_5 \quad (VIa)$$

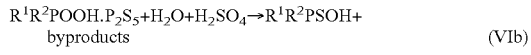

$$R^1R^2POOH.P_2S_5+H_2O+H_2SO_4 \rightarrow R^1R^2PSOH+ \text{byproducts} \quad (VIb)$$

$R^1$ and $R^2$ are each independently an alkyl radical having from 2 to 22 carbon atoms or as otherwise defined above.

In the step represented by Formula VIa, the $R^1R^2PO_2H$ was reacted with $P_2S_5$ in atmospheric pressure under anhydrous conditions, and then the solution was dissolved with diluted aqueous sulfuric acid in the step represented by Formula VIb. Then purified product was extracted with hexanes from the mixture resulting from the step represented by Formula VIb. In comparison with current commercial process to dialkylmonothiophosphinic acid, this process is much more cost efficient. The process utilizes no highly hazardous raw materials and does not require harsh reaction conditions such as high temperature and/or high pressure.

In particular to about 100 parts by weight bis(2,4,4-trimethylpentyl)phosphinic acid, preferably with 0 to 5 parts by weight sulfuric acid is vacuum dried in a reactor at 80 to 160° C. for 0.5 to 5 hours. Then the liquid is cooled to 20 to 100° C. About 15 to about 50 parts by weight phosphorus pentasulfide is then added. The mixture is stirred under nitrogen purge at 100 to 170° C. for 1 to 5 hours. By then almost all the solid is dissolved and a yellow-brown solution is obtained. Heating is continued for another 2 to 5 hours and then the mixture is cooled to 20 to 110° C. The batch was then dissolved with 20 to 100 parts by weight of 5% $H_2SO_4$ at 20 to 100° C. for 1 to 6 hours. To the dissolved mixture, 50 to 150 parts by weight hexanes are added and any solids are removed. The solids are presumably elemental sulfur. The aqueous phase is then replaced with 50 to 150 parts by weight of fresh 15% $H_2SO_4$ and the organic phase was dissolved at 50 to 100° C. for another 5 to 10 hours. The last procedure is repeated once more with 10% $H_2SO_4$. Afterwards, the organic phase is separated and washed with saturated aqueous sodium chloride solution. The bis(2,4,4-trimethylpentyl)monothiophosphinic acid is obtained after the solvent of hexanes is evaporated in vacuum.

In another respect, the present invention provides a process for converting dialkylmonothiophosphinic halide into dialkylmonothiophosphinic acid comprising: reacting dialkylmonothiophosphinic halide with water as follows:

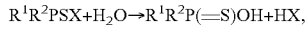

$$R^1R^2PSX+H_2O \rightarrow R^1R^2P(=S)OH+HX,$$

wherein X is a halogen, to form a mixture; wherein $R^1$ and $R^2$ are each independently an alkyl radical having from 2 to 22 carbon atoms or as otherwise defined above; and then acidifying the mixture with acid to extract dialkylmonothiophosphinic acid.

Typical halogens (X) are Cl, F, Br and/or I.

For example, the invention provides a preferred process for converting dialkylmonothiophosphinic chloride into dialkylmonothiophosphinic acid in an economical way by reaction with water under alkaline conditions as follows in Formula VII:

$$R^1R^2PSCl+OH^{-1} \rightarrow R^1R^2P(=S)OH+Cl^- \quad (VII).$$

$R^1$ and $R^2$ are each independently an alkyl radical having from 2 to 22 carbon atoms or as otherwise defined above.

In this respect, the present invention typically provides a process for converting monothiophosphinic chloride into dialkylmonothiophosphinic acid comprising reacting dialkylmonothiophosphinic chloride with a base at 20 to 100° C.

In particular, for example, 100 parts by weight of bis(2,4,4-trimethylpentyl)monothiophosphinic chloride may be reacted with from 30 to 100 parts of 50% sodium hydroxide in 30 to 200 parts of water at 25 to 100° C. for 1 to 5 hours. The so-obtained mixture is then neutralized with 15 to 50 parts of sulfuric acid. The product is then extracted with hexanes.

The present invention also provides a process for converting dialkylmonothiophosphinic halide into dialkyldithiophosphinic acid comprising reacting dialkylmonothiophosphinic halide with a sulfurizing agent to form the dialkyldithiophosphinic acid.

Typical halides are chloride, fluoride, bromide, and iodide.

Typical sulfurizing agents are hydrosulfides for example, NaHS, KSH, LiSH, Mg(SH)$_2$, Ca(SH)$_2$; sulfides for example Na$_2$S, K$_2$S. CaS, MgS, phosphorus sulfides for example P$_2$S$_5$, P$_4$S$_6$, P$_4$S$_7$; phosphorus oxysulfides, for example P$_2$O$_3$S$_2$, P$_2$O$_2$S$_3$; thiophosphates for example Na$_3$PS$_4$; and/or thiosulfates for example Na$_2$S$_2$O$_3$.

For example, the invention provides a preferred method for converting dialkylmonothiophosphinic chloride into dialkyldihiophosphinic acid in an economical way by reaction with sodium hydrogen sulfide and/or sodium sulfide as follows in Formula VIII:

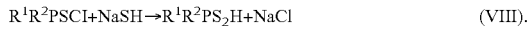

$$R^1R^2PSCl+NaSH \rightarrow R^1R^2PS_2H+NaCl \quad (VIII).$$

$R^1$ and $R^2$ are each independently an alkyl radical having from 2 to 22 carbon atoms or as otherwise defined above.

In this respect, the present invention provides a process for converting dialkylmonothiophosphinic chloride into dialkyldihiophosphinic acid comprising reacting dialkylmonothiophosphinic chloride with sodium hydrogen sulfide in water at 5 to 100° C.

In particular, for example, 100 parts by weight of bis(2,4,4-trimethylpentyl)monothiophosphinic chloride may be reacted with from 20 to 100 parts of sodium hydrosulfide hydrate in 20 to 100 parts of water at to 100° C. for 1 to 10 hours. The so-obtained mixture was then neutralized with 20 to 100 parts of sulfuric acid. The product is then extracted with hexanes.

The invention will now be described with reference to a specific example which is to be regarded solely as illustrative of the methods and compositions of this invention and not as restrictive of the scope thereof.

EXAMPLES

Example 1

To synthesize bis(2,4,4-trimethylpentyl)phosphinic acid, a 1.5 liter autoclave was charged with 40 g (0.377 moles) of sodium hypophosphite; 40 g of acetic acid; 132.3 g (0.943 moles) of diisobutylene (80%); and 2.8 g (0.019 moles) of tert-butyl peroxide initiator. The mixture was then heated to about 135° C. during an 8 hour day for about four days, i.e., a total of 30 hours and 1.4 g of the initiator was added at the beginning of each day. The reaction mixture was monitored by $^{31}$P NMR and resulted in the composition identified in TABLE I below. The original mixture contained 75.3% of the desired dialkylphosphinic acid product and 12.1% of the undesired monoalkylphosphinic acid by-product.

The completed reaction mixture (220 g) was transferred to an Erlenmeyer flask and heated in the range of from about 70° C. to about 80° C. to reduce the viscosity. 38 g of water was slowly added until two phases were observed. The aqueous phase was removed and its pH was measured to be about 5. The organic phase was then washed with 75 g of a 4% caustic solution and the resulting aqueous layer (89.2 g) was removed. The organic layer was acidified and washed with 50 g of a 10% sulfuric acid solution and the resulting aqueous phase removed.

The acidified and washed organic phase was filtered through PS paper and volatile materials were removed by vacuum distillation. 95 g of dialkylphosphinic acid product were recovered with a purity of 93.7% based on phosphorous NMR; thus a yield of 86.9%. The composition of the final product is identified in TABLE I below.

TABLE I

| Components | Initial Reaction Product Mixture (%) | Reaction Product Mixture After Purification (%) |
|---|---|---|
| Unreacted Hypophosphorus Acid | 1.6 | 0 |
| Monoalkylphosphinic Acid | 12.1 | 0 |
| Dialkylphosphinic Acid | 75.3 | 93.7 |
| Other Impurities | 11.0 | 6.3 |

From the above Example 1 and the detailed descriptions of the process in the body of this specification, it can be readily seen that the process of this invention permits the preparation of dialkylphosphinic acids, especially branched dialkylphosphinic acids of high purity in a simple manner with very good yields and therefore represents a significant advance in the industrial art.

Example 2

Example 2 demonstrates the preparation of dialkylmonothiophosphinic chloride.

In Example 2, Bis(2,4,4-trimethylpentyl)phosphinic acid prepared according to Example 1 (also known as IONQUEST 290 from Rhodia Inc.), 120 grams and thiophosphoryl chloride 70 grams were heated in a reaction vessel equipped with thermocouple, gas inlet, outlet, and stirrer under dry nitrogen at 120° C. for 3 hours. Then phosphorus pentasulfide 7.5 grams were added. The reaction temperature was increased to 140° C. over 1 hour and then kept at 130-140° C. for 3 to 4 hours. Precipitation occurred about 1 hour after phosphorus pentasulfide addition. After about 2 hours of reaction, 0.3 gram more of phosphorus pentasulfide was added and then excess thiophosphoryl chloride (14 grams) was stripped out of the reaction under slight vacuum. The batch was left to cool to room temperature and the liquid was decanted and the remaining product was washed out with hexanes to yield 111 grams of product. The product was pure by P-31. The solid was dissolved with 50 grams of 1% sulfuric acid in water and extracted with hexanes to yield 25 grams of a mixture of the product (42% by mole of Phosphorus) with other intermediates (58% by mole of Phosphorus). This mixture can be reused with fresh IONQUEST 290 dialkylphosphinic acid.

Example 3

Example 3 also demonstrates the preparation of dialkylmonothiophosphinic chloride with recycled material.

In Example 3, Bis(2,4,4-trimethylpentyl)phosphinic acid prepared according to Example 1 (also known as IONQUEST 290 from Rhodia Inc.), 100 grams and the mixture recovered from Example 2, 24 grams were heated to 135° C. under vacuum to dry for 2 hours in a reactor equipped with a thermocouple, gas inlet, outlet, and stirrer. The batch was cooled below 120° C. and then thiophosphoryl chloride 52.7 grams was added. Heating was continued for 2 hours at 120° C. By then 7.4 grams of phosphorus pentasulfide was added, the temperature was increased to 130° C. About 1.5 hours after phosphorus pentasulfide addition, excess thiophosphoryl chloride (about 2 grams) was removed from the reactor under slight vacuum. The heating was continued for another 2.5 hours. The batch was cooled to room temperature. Bis(2,4,4-trimethylpentyl)monothiophosphinic chloride 122 grams was decanted with 2 grams more obtained by extract the residual with hexanes (total yield 94%). The product was pure by P-31 NMR. 14 grams of materials was recovered after dissolving with 1% sulfuric acid by following the procedure in Example 2.

Example 4

This example demonstrates how to converts pure dialkylphosphinic acid into highly pure dialkylmonothiophosphinic acid in an economic way. Bis(2,4,4-trimethylpentyl)phosphinic acid prepared according to Example #1 (also known as IONQUEST 290), 22.5 grams and 97% sulfuric acid, 0.11 grams were vacuum dried in a reactor at 150° C. for 2 hours and then the liquid was cooled to 90° C. Phosphorus pentasulfide (7.2 grams) was added. The mixture was stirred under nitrogen purge at 155-160° C. for 4 hours, by then almost all the solid was dissolved and a yellow-brown solution was obtained. Heating was continued for another 3 hours and then cooled to 100° C. The batch was then dissolved with 10 grams of 5% $H_2SO_4$ at 65° C. for 4 hours. To the dissolved mixture, 20 grams of hexanes was added and a small of solid were removed, presumably elemental sulfur. The aqueous phase was then replaced with 20 grams of fresh 15% $H_2SO_4$ and the organic phase was dissolved for another 8 hours at 65-85° C. The last procedure was repeated once more with 10% $H_2SO_4$. Afterwards, the organic phase was separated and washed with saturated NaCl. The monothiophosphinic acid, 21 grams, was obtained after the solvent of hexanes was evaporated in vacuum. The product had purity of greater than 90% by P-31 NMR and 100% by gas chromatography.

Example 5

This example demonstrates the preparation of dialkylmonothiophosphinic acid from dialkylmonothiophosphinic chloride.

Bis(2,4,4-trimethylpentyl)monothiophosphinic chloride prepared according to examples 2 or 3 above 10 parts was stirred at 50-60° C. with 5.0 parts of 50% sodium hydroxide and 5 parts of water for 1 hour. A gel-like substance was separated from water. To this mixture, 3.6 parts of sulfuric acid was added. Stirring was continued until all gel was converted into liquid. The product was extracted with 20 grams of hexanes and 9.0 parts of product was recovered after solvent was evaporated. This product contained 73% mole of bis(2,4,4-trimethylpentyl)monothiophosphinic acid, 7% mole of bis(2,4,4-trimethylpentyl)phosphinic acid and 20% mole of pyro forms of bis(2,4,4-trimethylpentyl)monothiophosphinic acid.

Example 6

Example 6 demonstrates the preparation of dialkyldithiophosphinic acid from dialkylmonothiophosphinic chloride.

In this example, to bis(2,4,4-trimethylpentyl)monothiophosphinic chloride prepared according to examples #2 or #3 above 110 parts was mixed in 5 portions with 55 parts of 72% sodium hydrosulfide hydrate and 37 parts of water at 25-30° C. under cooling over 3.5 hour. After about 4 hours of reaction, more than 95% of the chloride was found to convert into product by P-31 NMR. The viscosity of the batch was built up. To facilitate the mixing, sulfuric acid 21 parts was added in two portions to reduce the viscosity. Sodium hydrosulfide hydrate (72%) 10 parts was added in three portions over 2 hours. The reaction temperature was continued at 25-30° C. for 1 more hour. To this mixture, 50 parts of 97% sulfuric acid was added. The product was extracted with 100 parts of hexanes twice. The organic solution was then washed with saturated sodium chloride and vacuum evaporated to yield 110 parts of product, which was measured by P-31 NMR to contain (by mole of phosphorus) 88% of bis(2,4,4-trimethylpentyl)dithiophosphinic acid and 7% of its disulfide dimeric and 1% bis(2,4,4-trimethylpentyl)monothiophosphinic acid and 4% non-reacted bis(2,4,4-trimethylpentyl)monothiophosphinic chloride as well as other minor unidentified impurities.

Example 7

Example 7 also demonstrates the preparation of dialkyldithiophosphinic acid from dialkylmonothiophosphinic chloride.

In this example, to bis(2,4,4-trimethylpentyl)monothiophosphinic chloride prepared according to Examples 2 or 3 above 122 parts was mixed with 20 parts 72% sodium hydrosulfide hydrate and 12 parts of water at 25° C. under cooling. Then 65 parts of 72% sodium hydrosulfide hydrate in seven portions were added to the reaction over 6 hours. During this period, 14 parts of 97% sulfuric acid in 40 part of water was added. The reaction was continued for another hour at 25° C. before the greenish yellow almost disappeared. To this mixture, 50 parts of 97% sulfuric acid was added. The product from the organic phase was measured by P-31 NMR to contain (by mole of phosphorus) 91% of bis(2,4,4-trimethylpentyl)dithiophosphinic acid and 8% of its disulfide dimeric and 1% bis(2,4,4-trimethylpentyl)monothiophosphinic acid and no non-reacted bis(2,4,4-trimethylpentyl)monothiophosphinic chloride.

Although this invention has been described in detail with particular reference to preferred embodiments thereof, it will be understood that variations and modifications can be effected within the spirit and scope of this invention as described hereinabove and as defined in the appended claims.

We claim:

1. A process for converting dialkylphosphinic acid into dialkylthiophosphinic halide comprising the step of:
   reacting $R^1R^2PO_2H$ with thiophosphoryl chloride and then with $P_2S_5$ to form dialkylthiophosphinic chloride, wherein $R^1$ and $R^2$ are each independently an alkyl radical having from 2 to 22 carbon atoms.

2. The process of claim 1, wherein the dialkylthiophosphinic chloride is a liquid and the process produces by-products which are solid at room temperature, further comprising isolating the product by separating the liquid product from the solid by-products.

3. The process of claim 1, wherein the by-products comprise non-converted intermediates, further comprising recovering the non-converted intermediates by dissolving the solid in water, extracting the non-converted intermediates with hexanes, vacuum drying the extracted non-converted intermediates and recycling the extracted non-converted intermediates to a reactor to be mixed with a mixture of $R^1R^2PO_2H$, thiophosphoryl chloride and $P_2S_5$.

4. The process of claim 1, further comprising forming the dialkylphosphinic acid by:
   a) reacting a hypophosphorous acid or salt with a stoichiometric excess of an alpha olefin in the presence of a free radical initiator to form a reaction product comprising monoalkylphosphinic acid and dialkylphosphinic acid;
   b) adding sufficient aqueous base to the reaction product to i) form the salts of the phosphinic acids, and ii) establish an aqueous phase and an organic phase, wherein a monoalkylphosphinic acid solubilizes into an aqueous phase;
   b) separating the organic phase from the aqueous phase;
   c) acidifying the organic phase;
   d) removing the olefin from the organic phase; and
   e) isolating the purified dialkylphosphinic acid product.

5. The process of claim 1, wherein the $R^1R^2PO_2H$ is reacted with thiophosphoryl chloride and then with $P_2S_5$ to form dialkylthiophosphinic chloride in atmospheric pressure under anhydrous conditions.

6. The process of claim 1, wherein the $R^1R^2PO_2H$ is reacted with thiophosphoryl chloride and then with $P_2S_5$ to form dialkylthiophosphinic chloride in atmospheric pressure under anhydrous conditions to form liquid dialkylthiophosphinic chloride.

7. A process for converting dialkylphosphinic acid into dialkylmonothiophosphinic halide comprising the step of:
   reacting $R^1R^2PO_2H$ with a sulfurizing agent and thiophosphoryl chloride to form a mixture,
   then dissolving the mixture with aqueous acid to form a reaction product; wherein $R^1$ and $R^2$ are each independently an alkyl radical having from 2 to 22 carbon atoms; and
   extracting a purified product from the reaction product by contacting the reaction product with a water-immiscible solvent,
   wherein the sulfurizing agent comprises a member of the group consisting of: $P_2S_5$, $P_4S_6$, $P_4S_7$, thiophosphoryl halides, $PSX_3$, wherein X is a halogen, $SX_2$, $S_2X_2$, $SF_6$, elemental sulfur with an oxidizing agent, $P_2O_3S_2$, and $P_2O_2S_3$.

8. The process of claim 7, wherein $R^1R^2PO_2H$ is reacted with $P_2S_5$ to form a mixture, wherein $R^1$ and $R^2$ are each independently an alkyl radical having from 2 to 22 carbon atoms; and
- then the mixture is dissolved with aqueous sulfuric acid to form a reaction product;
- and a purified product is extracted from the reaction product by contacting the reaction product with hexanes.

9. The process of claim 8, further comprising forming the dialkylphosphinic acid by:
- a) reacting a hypophosphorous acid or salt with a stoichiometric excess of an alpha olefin in the presence of a free radical initiator to form a reaction product comprising monoalkylphosphinic acid and dialkylphosphinic acid;
- b) adding sufficient aqueous base to the reaction product to i) form the salts of the phosphinic acids, and ii) establish an aqueous phase and an organic phase, wherein a monoalkylphosphinic acid solubilizes into an aqueous phase;
- b) separating the organic phase from the aqueous phase;
- c) acidifying the organic phase;
- d) removing the olefin from the organic phase; and
- e) isolating the purified dialkylphosphinic acid product.

10. The process of claim 8, wherein the $R^1R^2PO_2H$ is reacted with $P_2S_5$ in atmospheric pressure under anhydrous conditions.

* * * * *